(12) United States Patent
Perez et al.

(10) Patent No.: US 10,213,458 B2
(45) Date of Patent: Feb. 26, 2019

(54) DIFFERENTIAL TUMOR CELL CYTOTOXICITY VIA CONTACT WITH COATED CERIUM OXIDE NANOPARTICLES

(71) Applicants: Jesus Manuel Perez, Orlando, FL (US); Atul Asati, Orlando, FL (US); Santimukul Santra, Orlando, FL (US); Charalambos Kaittanis, New York, NY (US)

(72) Inventors: Jesus Manuel Perez, Orlando, FL (US); Atul Asati, Orlando, FL (US); Santimukul Santra, Orlando, FL (US); Charalambos Kaittanis, New York, NY (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 40 days.

(21) Appl. No.: 14/862,548

(22) Filed: Sep. 23, 2015

(65) Prior Publication Data

US 2016/0074334 A1    Mar. 17, 2016

Related U.S. Application Data

(62) Division of application No. 13/188,695, filed on Jul. 22, 2011, now abandoned.

(60) Provisional application No. 61/366,697, filed on Jul. 22, 2010.

(51) Int. Cl.
*A61K 9/50* (2006.01)
*A61K 33/24* (2006.01)
*A61K 9/51* (2006.01)

(52) U.S. Cl.
CPC .......... *A61K 33/24* (2013.01); *A61K 9/5138* (2013.01); *A61K 9/5161* (2013.01)

(58) Field of Classification Search
None
See application file for complete search history.

(56) References Cited

U.S. PATENT DOCUMENTS 8,236,284 B1 * 8/2012 Perez ................. A61K 49/0093
424/489

OTHER PUBLICATIONS

Tarnuzzer et al. "Vacancy Engineered Ceria Nanostrictures for Protection from Radiation-Induced Damage". 2005.*
Asati "Oxidase-Like Activity of Polymer-Coated Cerium Oxide Nanoparticles" Jan. 2009.*

* cited by examiner

*Primary Examiner* — Robert A Wax
*Assistant Examiner* — Danah Al-Awadi
(74) *Attorney, Agent, or Firm* — Timothy H. Van Dyke; Beusse, Wolter, Sanks & Maire PLLC

(57) ABSTRACT

Differential surface-charge-dependent localization of nanoceria in normal cells and cancer cells plays a critical role in the toxicity profile of a nanoceria particle. Engineered surface-coated cerium oxide nanoparticles with different surface charges that are positive, negative and neutral provide therapeutic results for normal and cancer cell lines. Results show that nanoceria with a positive or neutral charge enters most of the cell lines studied, while nanoceria with a negative charge internalizes mostly in the cancer cell lines. Moreover, upon entry into the cells, nanoceria is localized to different cell compartments (e.g. cytoplasm and lysosomes) depending on the nanoparticle surface charge. The internalization and subcellular localization of nanoceria plays a key role in the nanoparticle cytotoxicity profile, exhibiting significant toxicity when they localize in the lysosomes of the cancer cell lines. In contrast, minimal toxicity is observed when they localize into the cytoplasm or do not enter the cells.

2 Claims, 14 Drawing Sheets

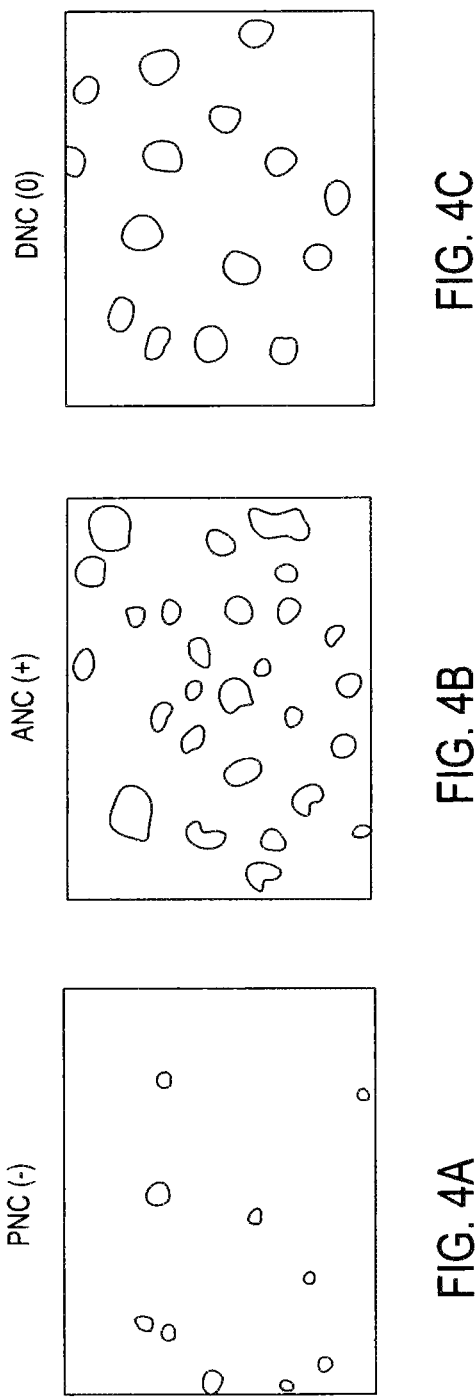

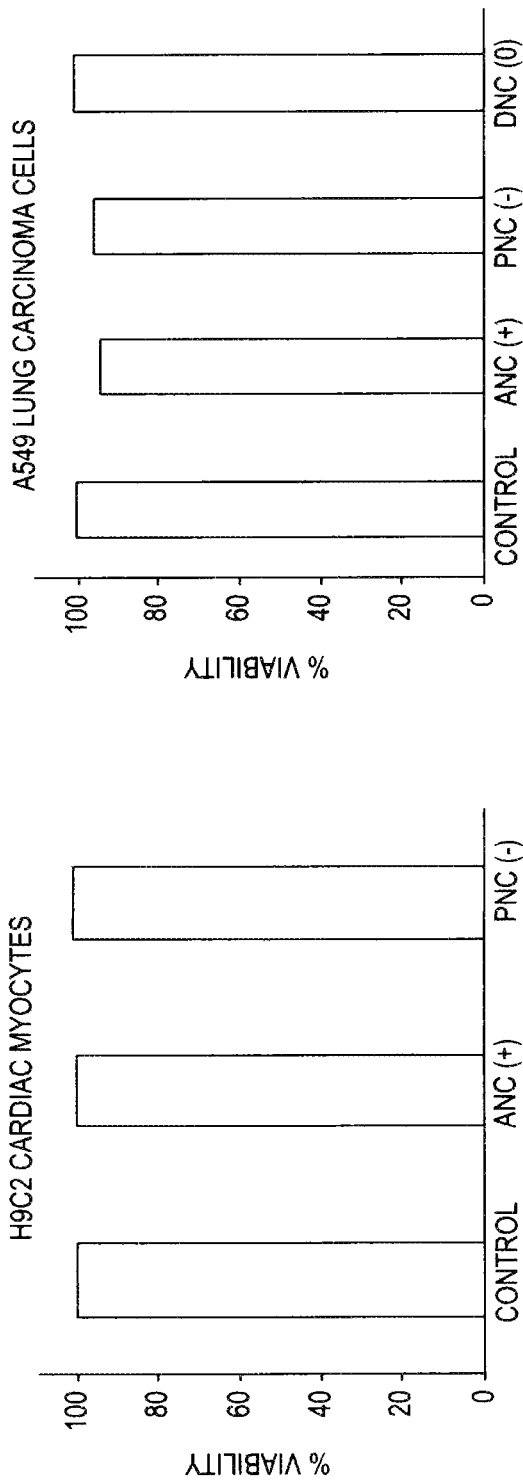

DIFFERENTIAL TUMOR CELL CYTOTOXICITY VIA CONTACT WITH COATED CERIUM OXIDE NANOPARTICLES

This application is a divisional of U.S. Ser. No. 13/188,695 filed on Jul. 22, 2011 which claims priority based on U.S. Provisional Patent Application Ser. No. 61/366,697 filed on Jul. 22, 2010, both of which are incorporated herein by reference.

The research herein is partially funded by the National Institutes of Health (NIH) under contract number CA10178.

FIELD OF THE INVENTION

This invention relates to polymer coated nanoceria particles and more particularly to treatment of human and animal cells wherein cell internalization and cytotoxicity of polymer-coated nanoceria plays a key role in the nanoparticle cytotoxicity profile, exhibiting significant toxicity when localized in the lysosomes of cancer cell lines.

BACKGROUND AND PRIOR ART

Nanomaterials with unique magnetic, luminescent and catalytic properties are being engineered for numerous biomedical applications, ranging from imaging, diagnostics and therapy, as reported in the following references: R. Weissleder, Molecular Imaging in Cancer. *Science* 2006, 312, 1168-1171; N. L. Rosi, N. L et al. Oligonucleotide-Modified Gold Nanoparticles for Intracellular Gene Regulation. *Science* 2006, 312, 1027-1030; M. Lewin et al, Tat peptide-derivatized Magnetic Nanoparticles Allow In vivo Tracking and Recovery of Progenitor Cells. *Nat Biotechnol* 2000, 18, 410-414; S. George et al., Use of a Rapid Cytotoxicity Screening Approach To Engineer a Safer Zinc Oxide Nanoparticle through Iron Doping. *ACS Nano* 2010, 4, 15-29; T. A. Xia et al., Polyethyleneimine Coating Enhances the Cellular Uptake of Mesoporous Silica Nanoparticles and Allows Safe Delivery of siRNA and DNA Constructs. *ACS Nano* 2009, 3, 3273-3286; Y. Roiter, et al., Interaction of Nanoparticles with Lipid Memberane. *Nano Lett* 2008, 8, 941-944; H. Vallhov, et al., Mesoporous Silica Particles Induce Size Dependent Effects on Human Dendritic Cells. *Nano Letters* 2007, 7, 3576-3582. However, the greatest strength of nanomaterial, which relies primarily on the enhanced physical and chemical characteristics that matter exhibits at this scale, has the potential to be its greatest liability.

Potentially harmful interactions can occur between nanomaterials and living systems, including systems in the human body. For this reason, nanomaterials must be engineered using materials that either are non-toxic, biocompatible and biodegradable or that have minimal and in some cases beneficial properties. An inflammatory response is a parameter that is often investigated to assess the effect that nanomaterials have within an organism, as reported by A. E. Nel et al, in Understanding Biophysicochemical Interactions at the Nano-bio Interface. *Nat Mater* 2009, 8, 543-557.

For instance, recent studies have shown that titanium oxide nanoparticles, which are widely used in cosmetics and skin care products, can elicit an inflammatory response and the generation of reactive oxygen species, causing DNA damage, according to B. C. Schanen et al., in Exposure to Titanium Dioxide Nanomaterials Provokes Inflammation of an In vitro Human Immune Construct. *ACS Nano* 2009, 3, 2523-2532 and A. A. Shvedova et al., in Exposure to Carbon Nanotube Material: Assessment of Nanotube Cytotoxicity using Human Keratinocyte Cells. *J Toxicol Environ Health A* 2003, 66, 1909-1926.

Also, single-walled carbon nanotubes can cause lipid peroxidation, oxidative stress, mitochondrial dysfunction and changes in cell morphology upon in vitro incubation with keratinocytes and bronchial epithelial cells, as discussed by C. W. Lam et al., in Histopathological Study of Single-Walled Carbon Nanotubes in Mice 7 and 90 days after Instillation into the Lungs. *Abstracts of Papers of the American Chemical Society* 2003, 225, U955-U955.

Furthermore, silver nanoparticles have been found to display size-dependent toxicity when exposed to alveolar macrophages via induction of oxidative stress, as reported by C. Carlson et al., in Unique Cellular Interaction of Silver Nanoparticles: Size-dependent Generation of Reactive Oxygen Species. *J Phys Chem B* 2008, 112, 13608-13619 and S. M. Hussain et al., in Safety Evaluation of Silver Nanoparticles: Inhalation Model for Chronic Exposure. *Toxicol Sci* 2009, 108, 223-224.

Quantum dots and fullerenes can also initiate an inflammatory response and the generation of reactive oxygen species, as discussed by H. H. Chen et al., in Acute and Subacute Toxicity Study of Water-Soluble Polyalkylsulfonated $C_{60}$ in Rats. *Toxicologic Pathology* 1998, 26, 143-151; H. H. Chen et al., in Renal Effects of Water-soluble Polyarylsulfonated C60 in Rats with an Acute Toxicity Study. *Fullerene Science and Technology* 1997, 5, 1387-1396 and A. Nel et al., in Toxic Potential of Materials at the Nanolevel, *Science* 2006, 311, 622-627.

Cerium oxide nanoparticle (nanoceria) is a unique nanomaterial, because it exhibits anti-inflammatory properties. Nanoceria has been found to scavenge reactive oxygen species (ROS), possess superoxide-dismutase-like activity, prevent cardiovascular myopathy, and provide radioprotection to normal cells from radiation as reported by the following references: J. M. Perez et al., in Synthesis of Biocompatible Dextran-coated Nanoceria with pH-dependent Antioxidant Properties. *Small* 2008, 4, 552-556; J. P. Chen et al., in Rare Earth Nanoparticles Prevent Retinal Degeneration Induced by Intracellular Peroxides. *Nature Nanotechnology* 2006, 1, 142-150; J. Niu et al., in Cardioprotective Effects of Cerium Oxide Nanoparticles in a Transgenic Murine Model of Cardiomyopathy. *Cardiovasc Res* 2007, 73, 549-559; R. W. Tarnuzzer et al., in Vacancy Engineered Ceria Nanostructures for Protection from Radiation-induced Cellular Damage. *Nano Lett* 2005, 5, 2573-2577; and C. Korsvik et al., in Vacancy Engineered Ceria oxide Nanoparticles Catalyze Superoxide Dismutase Activity, *Chemical Communications* 2007, 1056-1058.

The synthesis of biocompatible polymer-coated nanoceria with enhanced aqueous stability and unique pH-dependent antioxidant activity was recently reported by J. M. Perez et al. in *Small* 2008, 4, 552-556, supra. Particularly, it was found that nanoceria displays optimal antioxidant properties at physiological pH; whereas, it behaves as an oxidase at acidic pH, according to A. Asati et al., in Oxidase-Like Activity of Polymer-Coated Cerium Oxide Nanoparticles, *Angewandte Chemie-International Edition* 2009, 48, 2308-2312. Hence, this selective behavior may explain nanoceria's selective cytoprotection to normal cells, but not to cancer cells during radiation treatment or oxidative stress, as discussed by R. W. Tarnuzzer et al., in *Nano Lett* 2005, 5, 2573-2577, supra.

In addition, the nature of the polymeric coating surrounding the cerium oxide core could play a critical role in nanoceria's beneficial (antioxidant) vs harmful (oxidant)

properties. It was hypothesized that the cytotoxicity of cerium oxide nanoparticles could depend upon their subcellular localization. Once inside the cells, the nanoceria particle toxicity could depend on whether the particles are localized in particular cellular organelles, such as the lysosomes which are acidic, or distributed in the cytoplasm which is at neutral pH in normal cells. Since most tumors have an acidic microenvironment, this might switch off nanoceria antioxidant activity, turning on its oxidase activity and consequently sensitizing the tumor towards radiation therapy.

There is always a need for another weapon in the arsenal needed to fight disorders on a cellular level and the present invention provides the needed weaponry.

In the prior art, naked, bare nanoceria particles have been reported wherein the surface charge of the particle is modified. S. Patil et al. in "Protein Adsorption and Cellular Uptake of Cerium Oxide Nanoparticles as a Function of Zeta Potential" *Biomaterials*, 2007 November, 28 (31): 4600-4607 describes how surface chemistry of biomaterials have an impact on their performance. A. Vincent et al. in "Tuning Hydrated Nanoceria Surfaces: Experimental/Theoretical Investigations of Ion Exchange and Implications in Organic and Inorganic Interactions" *Langmuir*, 2010, 26 (10), 7188-7198 teaches that surface charge modified hydrated cerium oxide nanoparticles can be synthesized and provide detail of the dynamic ion exchange interactions with the surrounding medium. These surface charge modifications were based on the use of naked, bare, uncoated nanoceria particles.

Other research by C. Wilhelm in "Intracellular Uptake of Anionic Superparamagnetic Nanoparticles as a Function of Their Surface Coating" *Biomaterials*, 2003 24: 1001-1011 focused on the use of dextran-coated iron oxide nanoparticles to provide negative surface charges.

In co-pending U.S. patent application Ser. No. 12/704,678, with common inventors and common ownership, it is reported that polymer-coated nanoceria has intrinsic oxidase activity at acidic pH values and nanoceria behaves as an oxidant at pH 4. It is also reported that polymer-coated cerium oxide nanoparticles bind to folate expressing cancer cells and can be detected via catalytic oxidation of sensitive colorimetric substrates/dyes. The content of the co-pending U.S. patent application Ser. No. 12/704,678 is incorporated herein by reference.

In co-pending U.S. patent application Ser. No. 11/965,343, with common inventors and common ownership, a method for synthesizing non-toxic, biodegradable polymer coated nanoceria is disclosed. The polymeric-coatings discussed are at least one of a carbohydrate polymer, a synthetic polyol, a carboxylated polymer and derivatives thereof; the content of the co-pending U.S. patent application Ser. No. 11/965,343 is incorporated herein by reference.

A further co-pending U.S. patent application Ser. No. 12/169,179 with common inventors and common ownership, discloses polymer-coated nanoceria preparations that exhibit no toxicity to normal cells and exhibits pH-dependent antioxidant properties at neutral or physiological pH values and is inactive as an antioxidant at acidic pH values; the pH dependent properties of the polymer-coated nanoceria provides selective cytoprotection. The content of co-pending U.S. patent application Ser. No. 12/169,179 is incorporated herein by reference.

SUMMARY OF THE INVENTION

A first objective of the present invention is to provide a surface coating on nanoceria to modulate its differential cytotoxicity behavior in cancer versus normal cells.

A second objective of the present invention is to synthesize various nanoceria preparations coated with either a polymer or a small molecule.

A third objective of the present invention is to synthesize various nanoceria preparations coated with polyacrylic acid (PNC), aminated polyacrylic acid (ANC), or dextran (DNC) endowing the nanoparticles with a negative (−), positive (+) or neutral 0) surface charge, respectively.

A fourth objective of the present invention is to provide fluorescent modality to polymer-coated nanoceria, without compromising the solubility of the nanoparticles in aqueous media or reducing the number of available functional groups on the nanoparticle surface.

A fifth objective of the present invention is to encapsulate a dye, such as DiI, so that the polymer-coated nanoparticles can be used for intracellular tracking of the nanoparticles.

A sixth objective of the present invention is to design a nanoparticle wherein the surface charge thereon is modulated to one of at least a neutral charge, a positive charge and a negative charge to determine cytotoxicity for specific cell lines.

The objectives set forth above are met by the present invention which includes a plurality of surface-coated cerium oxide nanoparticles with a surface charge on each particle wherein the surface charge is selected from at least one of a positive charge, a negative charge and a neutral charge exhibiting differential cellular internalization and subcellular localization in cells selected from normal, non-transformed cells and malignant, transformed cells.

It is preferred that the plurality of surface-coated cerium oxide nanoparticles with a positive (+) surface charge are coated with aminated polyacrylic acid (ANC). It is also preferred that the plurality of surface-coated cerium oxide nanoparticles with a negative (−) surface charge are coated with polyacrylic acid (PNC). Another preferred surface coating for the plurality of cerium oxide nanoparticles provides a neutral (0) surface charge when coated with dextran (DNC) polymer.

It is also preferred that the plurality of polymer-coated cerium oxide nanoparticles further include an encapsulating dye within the hydrophobic microdomains of the polymeric coating on the surface of each nanoceria particle thereby fluorescently labeling the nanoparticles.

In the present invention, normal, non-transformed cells are isolated and selected from the group consisting of cardiac myocytes (H9c2) and human embryonic kidney cells (HEK293) and malignant, transformed cells are isolated and selected from the group consisting of lung carcinoma cells (A549) and breast carcinoma cells (MCF-7).

It is preferred that nanoceria particles with a positive (+) surface charge are internalized in isolated cells, selected from at least one of normal cardiac myocytes (H9c2), normal human embryonic kidney cells (HEK293) and malignant lung cells (A549). It is also preferred that polymer coated nanoparticles, with a positive surface charge are internalized in the normal cardiac myocytes (H9c2) and subsequently localized in the lysosome of each cell where the nanoparticle oxidase activity exhibits cytotoxicity.

In the present invention, polymer-coated cerium oxide nanoparticles, with a positive surface charge are internalized in normal human embryonic kidney cells (HEK293) and subsequently localized in the lysosome of each cell wherein the nanoparticle oxidase activity exhibits cytotoxicity. The polymer-coated cerium oxide nanoparticles, with a positive surface charge are also internalized in malignant lung cells (A549) and subsequently localized in the lysosome of each cell where the nanoparticle oxidase activity exhibits cytotoxicity.

It was also determined that the polymer-coated nanoparticles, with a positive surface charge are internalized in malignant breast tumor cells (MCF-7) and do not localize to the lysosome of each cell resulting in no cytotoxicity.

With regard to the plurality of surface-coated cerium oxide nanoparticles with a negative (−) surface charge, cell internalization occurred in normal cardiac myocytes (H9c2) and normal human embryonic kidney cells (HEK293) and subsequent subcellular localization also occurred in the cytoplasm of said normal cells and no cytotoxicity was displayed. It was also determined that the nanoparticle with a negative (−) surface charge undergoes cell internalization in malignant lung carcinoma cells (A549) and subcellular localization into the lysosomes of lung carcinoma cells (A549) and displays cytotoxicity.

A further determination was made that the nanoparticle with a negative (−) surface charge undergoes no cellular internalization in malignant breast carcinoma cells (MCF-7) and no subcelluar localization in malignant breast carcinoma cells (MCF-7) and displays no cytotoxicity.

Research shows that the plurality of surface-coated cerium oxide nanoparticles with a neutral (0) surface charge undergoes cell internalization in normal, non-transformed cells and malignant, transformed cells and subcellular localization in the cytoplasm of said cells and exhibits no toxicity.

A preferred pharmaceutical composition of the present invention includes a plurality of surface-coated cerium oxide nanoparticles and a carrier for selective cytotoxicity of malignant lung tumor cells.

Another preferred composition includes at least one cerium oxide nanoparticle; and a polymer coating bound to said cerium oxide nanoparticle, wherein said polymer coating provides a surface charge to said composition. It is preferred that the polymer coating is selected from at least one of polyacrylic acid that provides a negative surface charge to said composition, aminated polyacrylic acid that provides a positive surface charge, and dextran that provides a neutral surface charge.

The preferred composition further includes a fluorescent modality which is a dye encapsulated by said polymer coating; the preferred dye is 1,1′-dioctadecyl-3,3,3′3′-tetramethylindocarbocyanine perchlorate (DiI).

A preferred method for localizing at least one nanoparticle into at least one lysosome of at least one tumor cell includes providing at least one cerium oxide nanoparticle coated with a polymer coating, wherein said polymer coating provides a negative surface charge; exposing said cerium oxide nanoparticle to the tumor cell and contacting said tumor cell with the polymer-coated cerium oxide nanoparticle so that the nanoparticle is localized in the lysosome of the tumor cell providing a cytotoxic result.

Another preferred composition for intracellular localization of nanoparticles includes at least one cerium oxide nanoparticle, and at least one polymer coating bound to said nanoparticle, wherein said coating imparts a specific surface charge, said surface charge being dependant on a desired intracellular location. It is preferred that the polymer coating include polyacrylic acid, and said specific surface charge is negative, and said desired intracellular location is at least one lysosome.

It is also preferred that the polymer coating is dextran, and said surface charge is neutral, and the desired intracellular location is the cytoplasm. The preferred composition further includes a fluorescent modality comprising a dye encapsulated by said polymer coating wherein said dye is DiI.

A preferred method for intracellular localization of at least one nanoparticle includes providing at least one cerium oxide nanoparticle with a polymer coating, wherein said polymer coating has a specific surface charge, said charge depending on a desired intracellular location, and exposing the polymer coated cerium oxide nanoparticles to cells. When the polymer coating is polyacrylic acid, the specific surface charge is negative, and the desired intracellular location is at least one lysosome. It is also preferred that the polymer coating is dextran, said surface charge is neutral, and desired intracellular location is the cytoplasm.

Another preferred method for non-cytotoxic delivery of particles to cells includes providing at least one cerium oxide nanoparticle, wherein at least one polymer coating is bound to said cerium oxide nanoparticle, wherein said polymer coating provides a surface charge that is at least one of a positive charge and a neutral charge, and exposing the polymer-coated cerium oxide nanoparticle to at least one cell. A further polymer coating comprises dextran that provides the neutral charge; and another polymer coating includes aminated polyacrylic acid that provides a positive charge.

A preferred method for killing at least one tumor cell includes providing at least one cerium oxide nanoparticle coated with a polymer coating, wherein said polymer coating provides a negative surface charge, and exposing the cerium oxide nanoparticle to the tumor cell.

A preferred kit for treating cancer includes a quantity of cerium oxide nanoparticles coated with a polymer providing a surface charge, and at least one medical application device, wherein said medical application device and said nanoparticles are packaged together. It is preferred that the medical application device is selected from at least one syringe one topical applicator and one pill.

A preferred surface coated nanoceria particle with a neutral surface charge that is administered to a plurality of isolated normal and a plurality of isolated transformed cells and cellular uptake does not occur resulting in no toxicity to the normal and transformed cells.

Another surface coated nanoceria particle with a neutral surface charge that is administered to a plurality of isolated normal and a plurality of isolated transformed cells and cellular uptake does occur with subsequent subcellular localization in the cytoplasm of each normal and transformed cell resulting in no toxicity to the normal and transformed cells.

Further objects and advantages of this invention will be apparent from the following detailed description of a presently preferred embodiment, which is illustrated in the accompanying figures.

BRIEF DESCRIPTION OF THE FIGURES

FIG. 4A is a black and white line drawing of a confocal image of A549 lung carcinoma cells after treatment with PNC(−) coated nanoceria for 3 hours (3 h); PNC (−) coated nanoceria particles are uptaken by A549 lung carcinoma cells at a minimal level.

FIG. 4B is a black and white line drawing of a confocal image of A549 lung carcinoma cells after treatment with ANC(+) for 3 hours (3 h); positively charged particles are taken up by A549 lung carcinoma cell lines to a greater degree than the negatively charged or neutral charge coated nanoparticles.

FIG. 4C is a black and white line drawing of a confocal image of A549 lung carcinoma cells after treatment with DNC(0) coated nanoceria for 3 h; DNC(0) coated nanoceria is internalized in the A549 cells, in a manner suggesting that these coated nanoparticles are localized in the cytosol with a small fraction confined within the endosomal compartments.

FIG. 9A is a graph showing cytotoxicity of ANC(+) and PNC(−) coated cerium oxide nanoparticles on H9c2 cardiac myocytes in the presence of an endocytosis inhibitor; no toxicity was measured.

FIG. 9B is a graph showing cytotoxicity of ANC(+), PNC(−) and DNC(0) coated cerium oxide nanoparticles on A549 lung carcinoma cells in the presence of an endocytosis inhibitor; no significant toxicity measured.

DESCRIPTION OF THE PREFERRED EMBODIMENT

Figure 1:
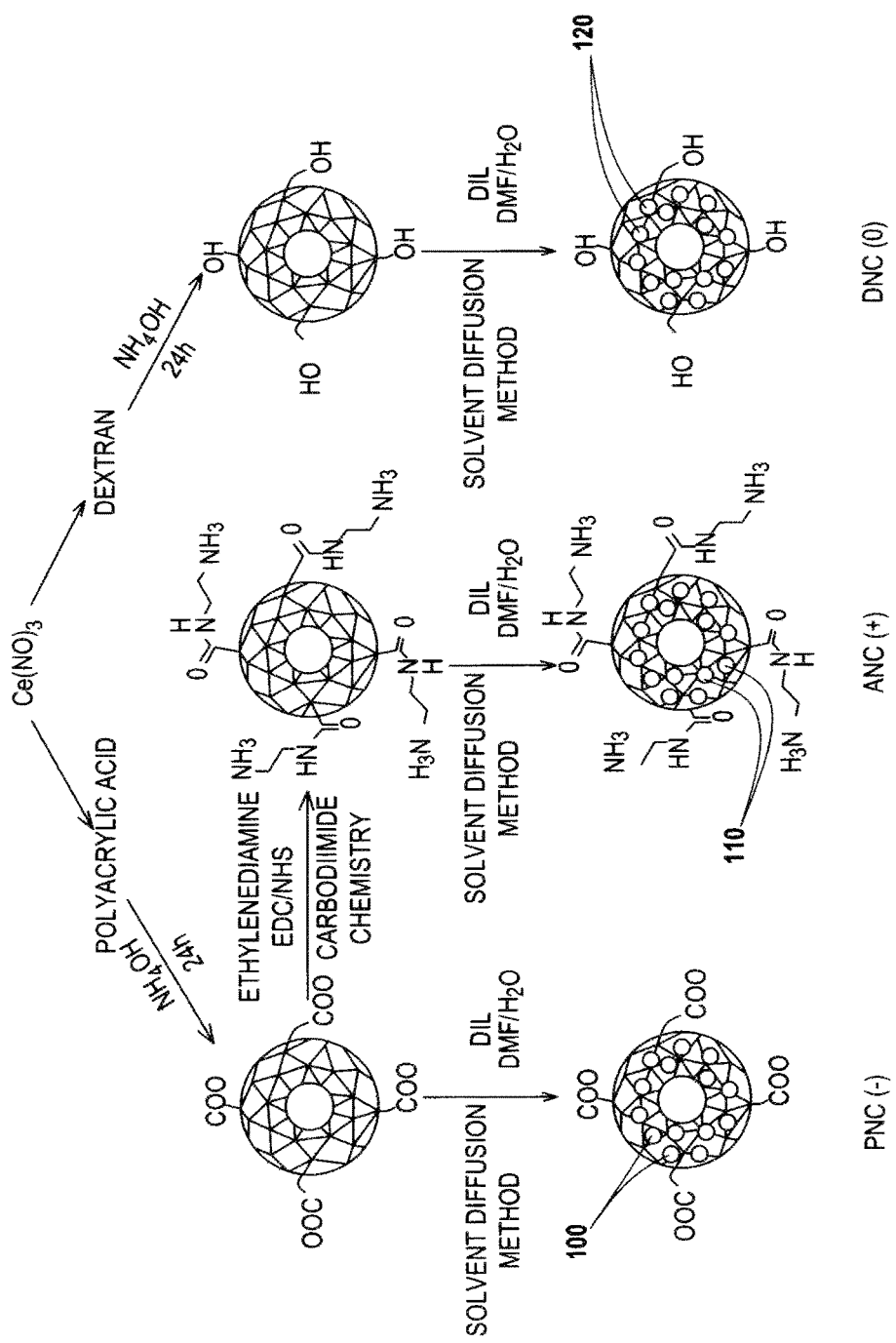
FIG. 1 shows surface functionalization of cerium oxide nanoparticles wherein cerium oxide nanoparticles with different polymer coatings and surface modifications yield nanoparticles with a negative [PNC(−)], a positive [ANC(+)], and a neutral [DNC(0)] charge. A fluorescent dye (DiI), 100, 110, 120 was encapsulated using a modified solvent diffusion method.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words and acronyms used herein and their application before discussing the composition of matter and method of using and making the same.

A549 is used to identify lung carcinoma cells

ANC(+) is used herein to mean an aminated polymer-coated nanoceria particle with a positive charge on the surface of the particle.

DiI is a fluorescent dye with the chemical name, 1,1'-dioctadecyl-3,3,3'3'-tetramethylindocarbocyanine perchlorate.

DNC(0) is used herein to mean a dextran polymer-coated nanoceria particle with a neutral charge on the surface of the particle.

H9c2 is used to identify cardiac myocyte cells

HEK293 stands for human embryonic kidney cells

IONP(+) is used herein to mean a polymer coated iron oxide nanoparticle with a positive charge on the surface of the particle.

IONP(−)] is used herein to mean an aminated polymer coated iron oxide nanoparticle with a negative charge on the surface of the particle.

MCF-7 is used to identify breast carcinoma cells PNC(−) is used herein to mean a polyacrylic acid coated nanoceria particle with a negative charge on the surface of the particle.

Surface coatings on nanoceria particles are disclosed herein as polymeric coatings; however, the coatings can comprise small molecules, such as amino acids, small cyclical polyols such as cyclodextrins, and simple sugars. Thus, the examples and discussion herein based on polymeric-coatings should not be considered as limiting. The criteria for a suitable coating for the present invention is one that adheres to the surface of the nanoceria particle, provides a surface charge for the nanoceria particle and at the same time modulates the cytotoxicity of the resulting coated nanoceria nanoparticle.

In the present invention, a novel use of a polymer's surface-charge-dependent cell internalization and cytotoxicity profile of cerium oxide nanoparticles in normal versus malignant cells is reported. Various cell lines were selected in order to assess the corresponding behavior of cerium oxide nanoparticles. Cardiac myocytes (H9c2) and human embryonic kidney (HEK293) cells were selected as non-transformed (normal) cells, whereas lung (A549) and breast (MCF-7) carcinomas were selected as transformed (cancer) cell lines.

Except for breast carcinoma cells, results show that positively charged nanoceria particles internalize in other cells, localize preferentially in lysosomes and subsequently become toxic to these cells. With regard to polymer-coated nanoceria with a negative charge, it was internalized and localized into the lysosomes of lung carcinoma (A549) cells only, but not by the lysosomes of breast carcinoma cells (MCF-7), thus exhibiting toxicity only to the lung carcinoma cells.

Also, the negatively charged polymer-coated nanoceria particles were not internalized and therefore were not toxic to the normal cells, including, but not limited to, cardiac myocytes and human embryonic kidney cells. Surprisingly, nanoceria with a neutral charge was not toxic to normal cells or cancer cells, as these nanoparticles primarily localized in the cytoplasm of these cells. The combined results suggest that the internalization and subcellular localization of polymer-coated nanoceria plays a critical role in the toxicity profile of this nanomaterial. The results herein also suggest that the coating on nanoceria can be engineered in order to modulate its differential cytotoxicity behavior in cancer versus normal cells.

Example 1—Synthesis and Characterization of Polymer-Coated Cerium Oxide Nanoparticles FIG. 1 is an illustration of various nanoceria preparations coated with either polyacrylic acid (PNC), aminated polyacrylic acid (ANC), or dextran (DNC) that endow nanoparticles with a negative (−), positive (+) or neutral (0) surface charge, respectively.

During synthesis, the nanoparticles were labeled fluorescently, by encapsulating a dye (DiI) 100, 110, 120 within the hydrophobic microdomains of the polymeric coatings of each nanoceria preparation, following a previously reported solvent diffusion methodology disclosed by S. Santra in Drug/dye-loaded, Multifunctional Iron oxide Nanoparticles for Combined Targeted Cancer Therapy and Dual Optical/Magnetic Resonance Imaging, *Small* 2009, 5, 1862-1868.

Figures 2A, 2B:
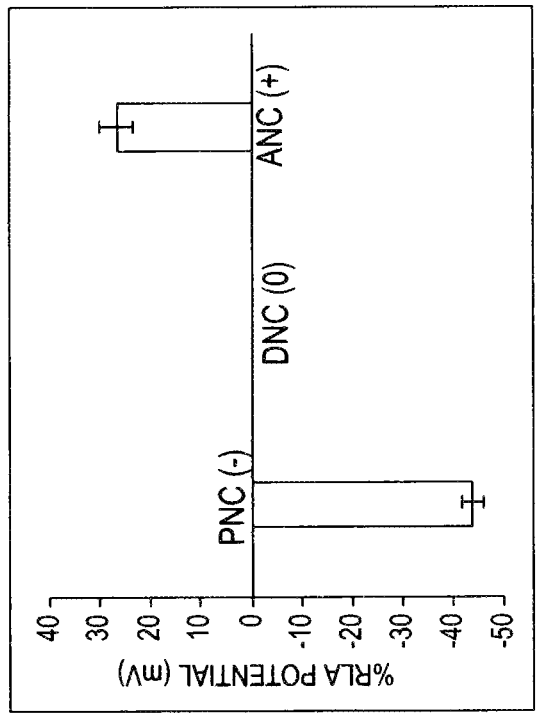
FIG. 2A is a chart of the size of a cerium oxide nanoparticle core measured by transmission electron microscopy (TEM).
FIG. 2B is a graph of the Zeta potential of cerium oxide nanoparticles with different surface functionalities: negative, neutral and positive.

Transmission electron microscopy (TEM) studies reported in FIG. 2A show the presence of nanoparticles of similar core size (3 to 4 nm) in all preparations as reported by A. Asati, et al., in *Angewandte Chemie-International Edition* 2009, 48, 2308-2312, supra. While dynamic light scattering experiments, show the presence of monodisperse nanoceria preparations with average hydrodynamic diameter of 14 nm for DNC(0) and 5 nm for both PNC (+) and ANC(+).

The presence of different surface charges in the various nanoceria preparations was assessed by zeta potential as shown in FIG. 2B, confirming the presence of a negative, neutral and positive charge for PNC, DNC and ANC, respectively. FT-IR analysis further confirmed the nanoparticle polymer surface coating and functionality in FIG. 2C.

Figure 2D:
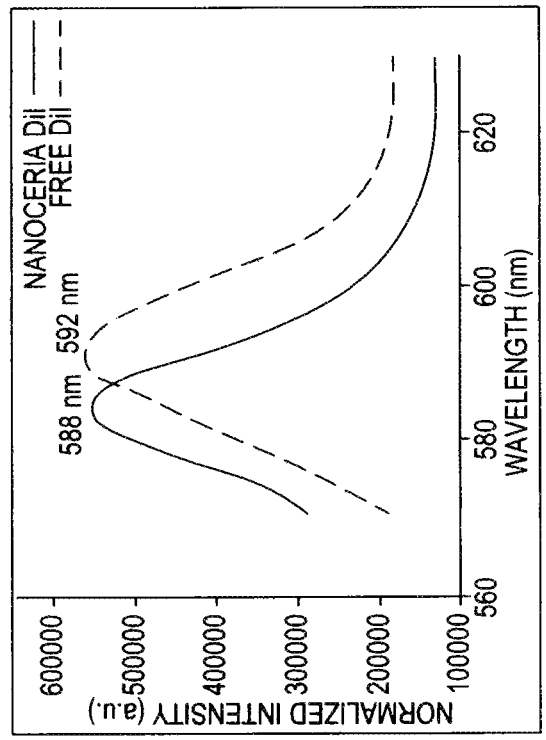
FIG. 2D is the fluorescence emission spectra of the DiI-encapsulating nanoceria and free dye DiI.
Figure 2C:
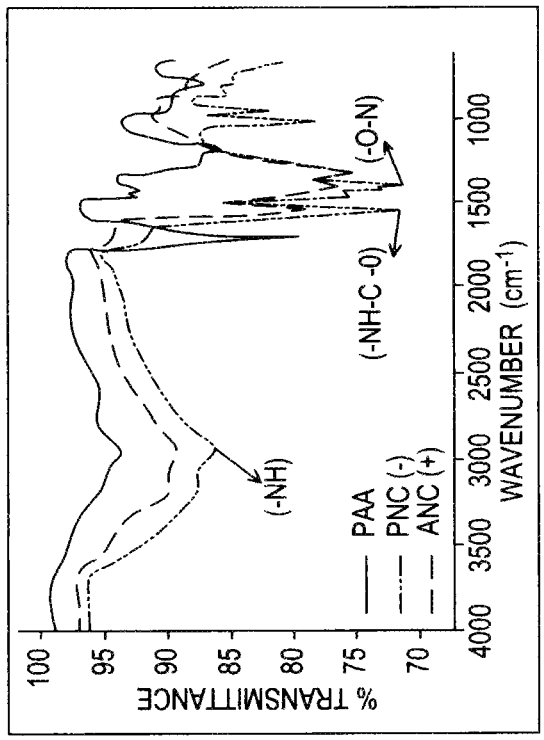
FIG. 2C is the FT-IR spectra of the carboxylated (negative) and aminated (positive) surface group on nanoceria.

When using the methodology reported by S. Santra in *Small* 2009, 5, 1862-1868 supra, fluorescent modality was introduced to the polymer-coated nanoceria, without compromising the solubility of the nanoparticles in aqueous media or reducing the number of available functional groups on the nanoparticle surface. Successful encapsulation of DiI into the nanoceria was confirmed via fluorescence spectroscopy, where a blue shift in the DiI-encapsulating ceria nanoparticles (584 nm) emission spectrum was observed as opposed to free DiI (592 nm) as shown in FIG. 2D. The DiI-encapsulating polymer-coated-nanoceria displayed good aqueous stability over long periods of time without significant release of the dye, and can be used for the intracellular tracking of the nanoparticles.

Thus, surface functionalization of cerium oxide nanoparticles as shown in FIG. 1 occurs during the synthesis of the polymer-coated nanoparticles via a solvent diffusion method.

Example 3—Surface-Charge-Dependent Cellular Interaction of Nanoceria

Confocal microscopy experiments were performed in order to study the cellular uptake and intracellular localizaton of the DiI-labeled polymer-coated nanoceria. In these experiments, PNC (−), ANC (+) and DNC(0) (1.0 mM) were incubated with two transformed carcinoma cell lines (A549 lung and MCF-7 breast carcinomas), and two non-transformed (normal) cell lines (H9c2 cardiac myocytes and HEK293 human embryonic kidney cells). These cells lines were selected in order to investigate whether there is a difference in uptake by ANC(+), PNC(−) and DNC(0) polymer-coated nanoparticles, thus potentially displaying different toxicity profiles.

Figure 3C:
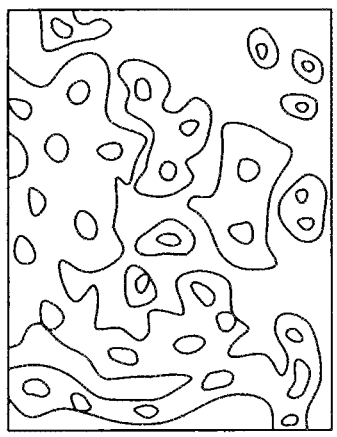
FIG. 3C is a black and white line drawing of a confocal image showing uptake of DNC(0) coated cerium oxide nanoparticles (nanoceria) by normal H9c2 cardiac myocyte cells; diffused cytoplasmic localization with internalization in H9c2 is shown by interconnected irregular shapes.
Figure 3B:
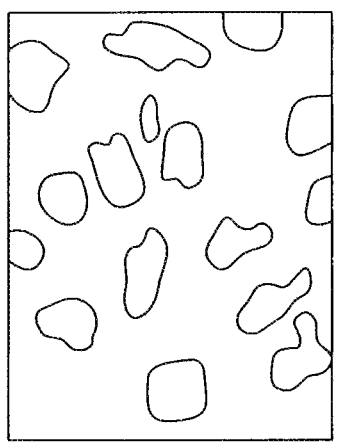
FIG. 3B is a black and white line drawing of a confocal image showing uptake of ANC (+) coated cerium oxide nanoparticles (nanoceria) by normal H9c2 cardiac myocyte cells; uptake observed is shown by irregular shapes.
Figure 3A:
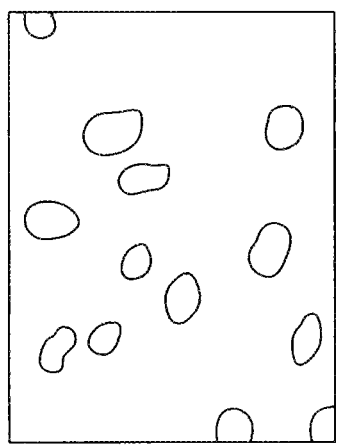
FIG. 3A is a black and white line drawing of a confocal image showing uptake of PNC (−) coated cerium oxide nanoparticles (nanoceria) by normal H9c2 cardiac myocyte cells; minimal uptake is observed.

First, the internalization pattern of ANC(+), PNC(−) and DNC(0) was studied in normal cardiac myocyte cells (H9c2), using 10,000 cells as shown in FIGS. 3A-3C. After a 3-hour incubation, results showed that the negatively charged carboxylated nanoparticles [PNC(−)] were minimally uptaken by the H9c2 cardiac myocyte cells and did not internalize in the H9c2 cell line as shown in FIG. 3A.

The positively charged aminated nanoparticles [ANC(+)] were uptaken by the H9c2 cardiac myocytes, as indicated by the elevated cell-associated fluorescence in the H9c2 cells as shown by irregular shapes in FIG. 3B.

The neutral dextran-coated nanoparticle [DNC(0)] shows a higher degree of internalization in the H9c2 cells as shown in FIG. 3C. Interestingly, the DNC(0) intracellular fluorescence pattern in the H9c2 cells was diffused, showing a different pattern from the ANC(+) punctuated fluorescence pattern. This difference seems to indicate a unique nanoparticle surface-charge dependent internalization mechanism with different intracellular compartmentalization into the cytoplasm among the nanoparticles studied in the non-transformed cell line.

Example 4—Internalization Experiments with Cancer Cells

FIGS. 4A-4C show results of internalization experiments performed with cancer cells (10,000 cells) derived from lung (A549) carcinoma cells. PNC(−) uptake by the A549 cells is minimal or slight as shown in FIG. 4A. In FIG. 4B, lung (A549) carcinoma cells were able to uptake ANC (+); interestingly, a higher degree of internalization and pronounced punctuated fluorescence was observed with the ANC(+) in the A549 cells. This might indicate that in these cells the majority of the ANC(+) localized into endosomal compartments. In contrast, in FIG. 4C, minimal and diffused intracellular fluorescence was observed with the DNC(0) in the A549 cells, suggesting that these nanoparticles are mostly localized in the cytosol with a small fraction confined within the endosomal compartments. Taken together, the above results suggest that the surface charge on polymer-coated nanoceria dictates their differential internalization and localization in normal cells (FIGS. 3A-3C) versus cancer cells (FIGS. 4A-4C).

Example 5—Intracellular Distribution of Polymeric Cerium Oxide Nanoparticles To corroborate that after internalization some of the polymer-coated nanoceria localized in endosomal compartments, we first treated the cells (10,000 cells) for 3 h with the PNC(−), ANC(+) and DNC(0) (1.0 mM) followed by a 20-minute treatment with Lysotracker (35 nM), a lysosome specific dye. Lysotracker is a green fluorescent dye that stains the acidic lysosomes, hence the potential co-localization between DiI-labeled-nanoceria (red) and lysosomes (green) should yield a yellow/orange overlap when the images are merged.

Experiments were carried out with A549 lung carcinoma cells. Results showed that DiI-labeled-ANC(+) and DiI-labeled-PNC(−) co-localized with Lysotracker in the A549 lung cancer cells, as determined by confocal microscopy images shown in FIGS. 5A-5B. Even though less internalization of DiI-labeled-PNC(−) is observed in these cells, the internalized nanoparticles predominantely co-localized mostly with the Lysotracker dye indicating lysosomal localization.

Figure 5C:
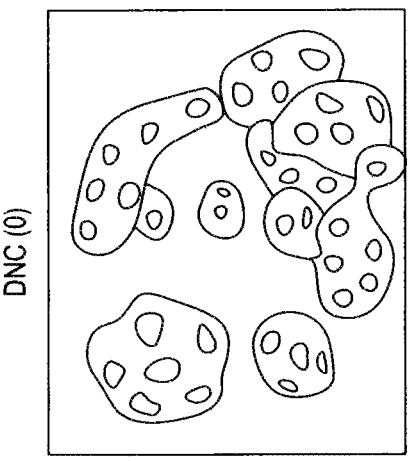
FIG. 5C is a black and white line drawing of a confocal image of DNC(0) coated nanoceria intracellular localization in lung carcinoma cells (A549); on internalization, the neutral nanoceria [DNC(0)] localizes mostly in the cytoplasm.
Figure 5B:
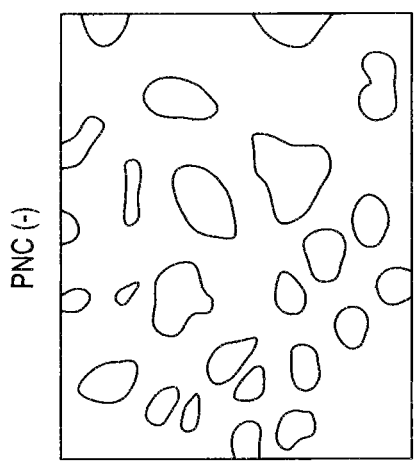
FIG. 5B is a black and white line drawing of a confocal image of PNC(−) coated nanoceria intracellular localization in lung carcinoma cells (A549); on internalization, the negatively charged [(PNC (−)] nanoceria co-localizes with the lysosome.
Figure 5A:
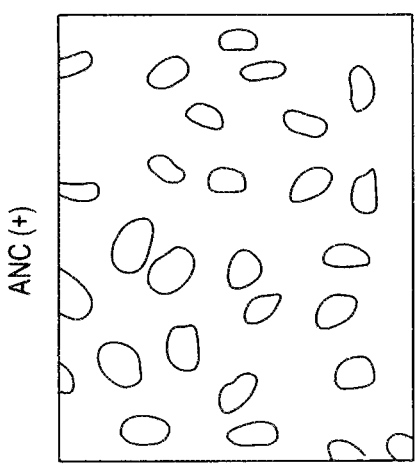
FIG. 5A is a black and white line drawing of a confocal image of ANC(+) coated nanoceria intracellular localization in lung carcinoma cells (A549); on internalization, the positively charged [ANC (+)] nanoceria co-localizes with the lysosome.

In contrast, DiI-labeled-DNC(0) showed a diffused distribution with minimal localization in the lysosomes of A549 cells as shown in FIG. 5C. The results in Example 5 demonstrate that the surface charge on the ceria nanoparticles dictates the subcellular localization of nanoceria in cancer cells.

Example 6—Determination of the Oxidase-Like Activity of Lysosome-Residing Nanoceria Nanoceria has been reported by A. Asati et al., in *Angewandte Chemie-International Edition* 2009, 48, 2308-2312, supra to possess unique oxidase-like activity at acidic pH, oxidizing various colorimetric substrates, such as 3,3', 5.5'-tetramethylbenzidine (TMB) and 2,2-azino-bis(3-ethylbenzothizoline-6-sulfonic acid (AzBTS). This activity can be employed to assess the localization of nanoceria in various cell organelles, particularly lysosomes, via the nanoparticle's oxidase activity, using TMB as the colorimetric substrate.

Figure 6B:
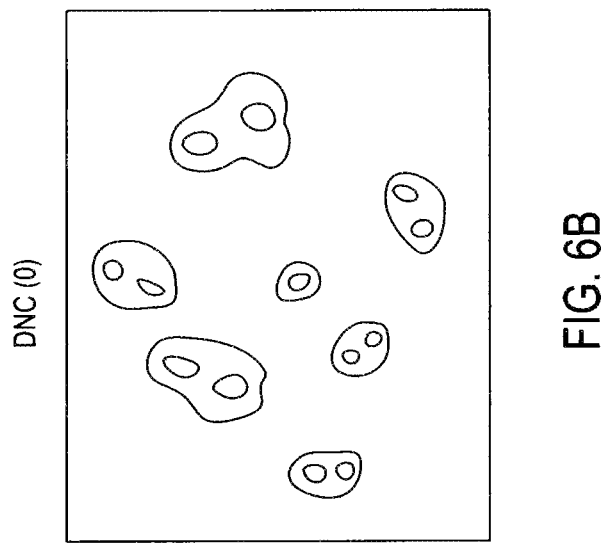
FIG. 6B is a black and white line drawing of a confocal image of DNC(0) coated nanoceria intracellular localization in cardiac myocytes (H9c2); on internalization, the neutral nanoceria [DNC(0)] does not co-localize significantly to the lysosomes with most of the nanoparticles localizing to the cytoplasm.
Figure 6A:
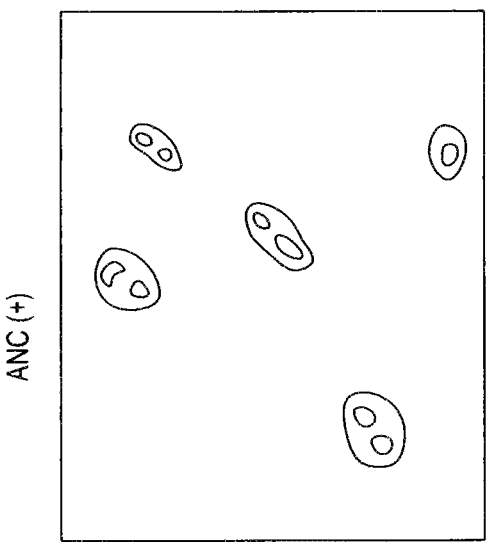
FIG. 6A is a black and white line drawing of a confocal image of ANC (+), coated nanoceria intracellular localization in cardiac myocytes (H9c2); on internalization, the posivitely charged [ANC (+)] is found in both the cytoplasm and lysosomes.

Hence, to further confirm that some of the polymer-coated cerium oxide nanoparticles localized into the lysosomes, cells were incubated with the different nanoceria preparations for 3 hours, followed by lysosomal isolation. Then, the oxidase activity of the isolated lysosomes was determined spectrophotometrically via TMB oxidation. As expected and in agreement with the microscopy and lysosomal co-localization experiments, we found that ANC(+) coated nanoceria particles were mostly entrapped within the lysosome of the H9c2 cardiac myocyte cell lines, as the lysosomes isolated from these cells exhibited significant levels of oxidase activity as shown in FIG. 6A.

On internalization, the positively charged ANC(+) coated nanoceria is found in both the cytoplasm and lysosomes. In contrast, neutral nanoceria with DNC(0) coating does not significantly co-localize to the lysosomes with most of the nanoparticles found in the cytoplasm as observed in FIG. 6B.

Referring now to FIGS. 7A-7D, lysosomal isolation and determination of oxidase-like activity of entrapped polymer-coated nanoceria is reported. In agreement with the microscopy and lysosmal co-localization experiments, it was determined that ANC(+) coated nanoceria were mostly entrapped within the lysosome of the H9c2, HEK293 and A549 cell lines, as lysosomes isolated from these cells exhibited significant levels of oxidase activity as shown in FIGS. 7 A-7C.

Figure 7B:
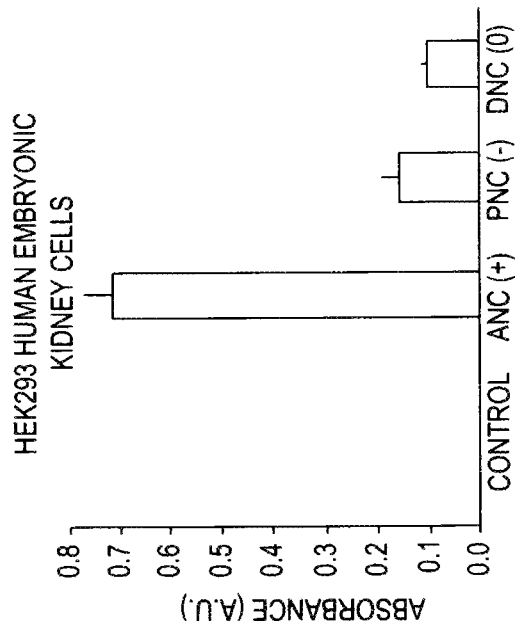
FIG. 7B is a graph of ANC(+), PNC(−) and DNC(0) coated lysosomal isolation and determination of the oxidase-like activity of nanoceria in HEK293 human embryonic kidney cell lines; the ANC (+) coated nanoparticles are mostly entrapped into lysosomes, based on the presence of significant oxidase activity in the lysosomes isolated from these cells lines after incubation with ANC (+).
Figure 7A:
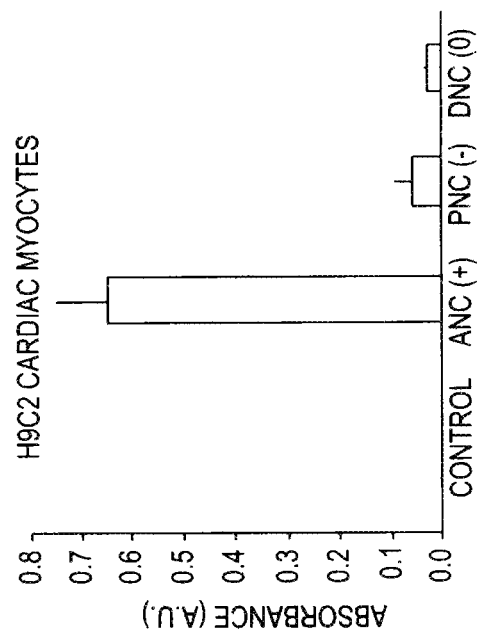
FIG. 7A is a graph of lysosomal isolation and determination of the oxidase-like activity of ANC(+), PNC(−) and DNC(0) coated nanoceria in H9c2 cardiac myocyte cell lines; the ANC (+) coated nanoparticles are mostly entrapped into lysosomes, based on the presence of significant oxidase activity in the lysosomes isolated from these cells lines after incubation with ANC (+).
Figures 7C, 7D:
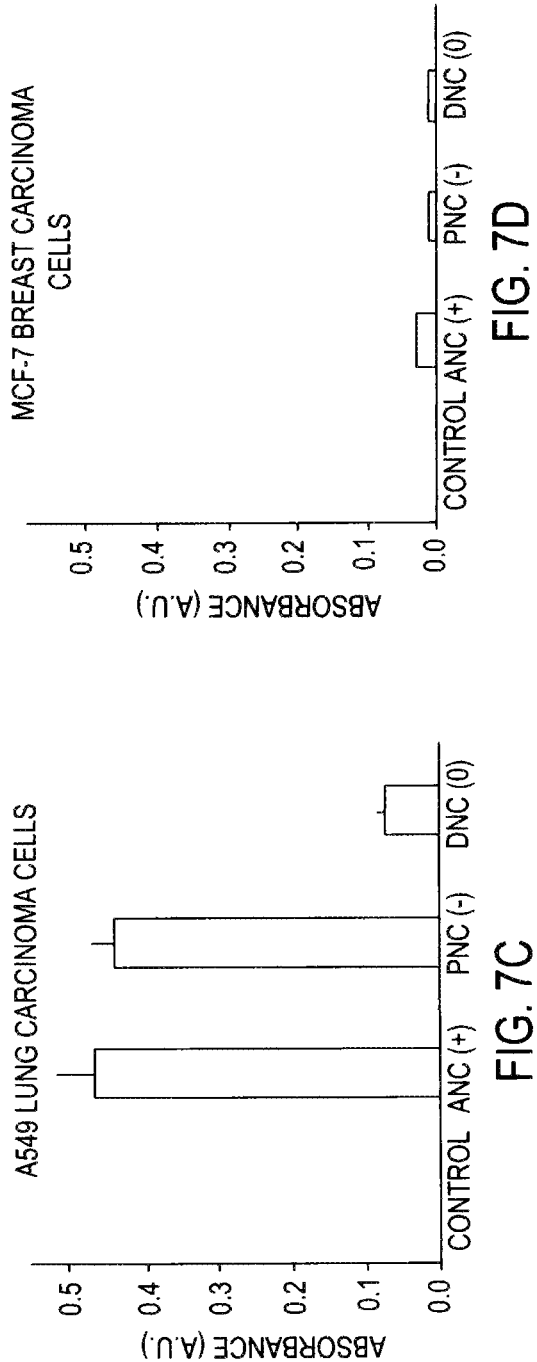
FIG. 7C is a graph of lysosomal isolation and determination of the oxidase-like activity of ANC(+), PNC(−) and DNC(0) coated nanoceria in A549 lung carcinoma cell lines; the ANC (+) and PNC(−) coated nanoparticles are mostly entrapped into lysosomes, based on the presence of significant oxidase activity in the lysosomes isolated from these cells lines after incubation with ANC (+) and PNC(−) coated nanoceria.
FIG. 7D is a graph of lysosomal isolation and determination of the oxidase-like activity of ANC(+), PNC(−) and DNC(0) coated nanoceria in MCF-7 breast carcinoma cell lines; the ANC (+), PNC(−) and DNC(0) coated nanoparticles are not internalized or not entrapped into lysosomes. In the absence of significant oxidase activity in the lysosomes isolated from these MCF-7 breast cancer cells lines after incubation with ANC (+), PNC(−) and DNC(0) coated nanoceria, there was no toxicity to the MCF-7 breast cancer cell lines.

In MCF-7 breast carcinoma cell line, no localization to the lysosomes was observed as these cells do no uptake any of the nanoparticles as shown in FIG. 7D.

Interestingly, when cells were incubated with PNC(−), only the lysosomes isolated from A549 lung carcinoma cells (FIG. 7C) exhibited oxidase activity based on the lysosomal co-localization experiments. Meanwhile, the lysosomes from cells incubated with the DNC(0) exhibit minimal oxidase activity, corroborating the confocal microscopy studies. Lysosomes isolated from untreated cells (H9c2, HEK293, A549 and MCF-7) did not possess any oxidase activity (control), as indicated by the absence of TMB oxidation shown in FIGS. 7A-7D, and confirming the absence of endogenous oxidase activity in these organelles.

In H9c2 and HEK293 cell lines, the ANC (+) nanoparticles are mostly localized into lysosomes, judging by the presence of significant oxidase activity in the lysosomes isolated from these cells lines after incubation with ANC (+) as shown in FIG. 7A and FIG. 7B, respectively. PNC (−) and DNC(0) treated cells showed minimal oxidase activity in their lysosomes as shown in FIGS. 7A, 7B and 7D. In A549, oxidase activity was detected in cells treated with ANC (+) and PNC(−), while minimal activity was present in the DNC(0) treated cells (FIG. 7C).

The lysosomes isolated from MCF-7 cells treated cells did not show significant oxidase activity as the polymer-coated nanoceria does not internalized in these cell lines (FIG. 7D). Lysosomes isolated from non-treated cells do not show any oxidase activity.

Example 8—Intracellular-Distribution-Dependent Cytotoxicity of Polymeric Cerium Oxide Nanoparticles In order to determine if the surface-charge-dependent internalization and intracellular (lysosomal vs cytoplasmic) localization of the polymer-coated nanoceria plays a role in the nanoparticle cytotoxicity, cell viability (MTT) assays were performed. Interestingly, we found that DNC(0) did not exhibit any toxicity to the cell lines studied (FIGS. 8A-8D), as most of these nanoparticles localized to the cytoplasm. Furthermore, prolonged incubation of these cell lines with the dextran-coated-nanoceria did not affect cell morphology and proliferation ability as previously reported by J. M. Perez et al., in *Small* 2008, 4, 552-556, supra.

Figure 8B:
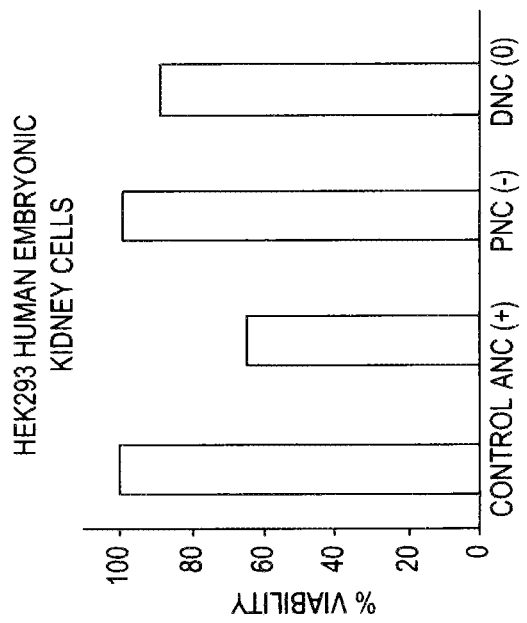
FIG. 8B is a graph showing cytotoxicity of ANC(+), PNC(−) and DNC(0) coated cerium oxide nanoparticles to HEK293 human embryonic kidney cells.
Figure 8A:
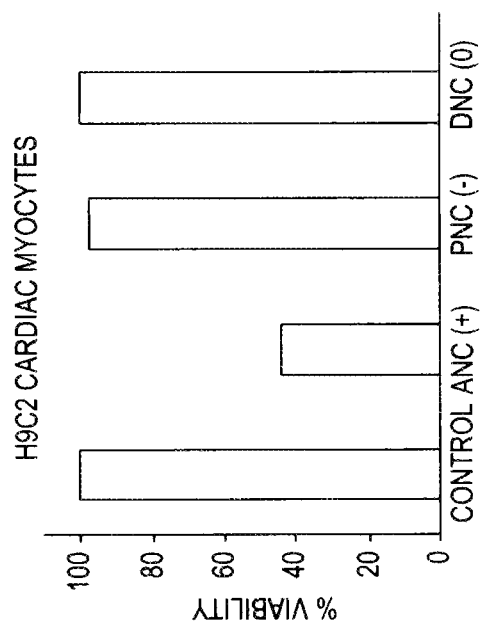
FIG. 8A is a graph showing cytotoxicity of ANC(+), PNC(−) and DNC(0) coated cerium oxide nanoparticles to H9c2 cardiac myocyte cells.

In contrast, ANC(+) and PNC(−) had different degrees of toxicity, depending on the nanoparticle's localization inside the cell. For instance, the PNC(−) nanoparticles were not toxic to the H9c2 cardiac myocytes or the HEK293 kidney cells as shown in FIGS. 8A and 8B, respectively. PNC(−) coated nanoceria particles were toxic to the A549 lung carcinoma cells (FIG. 8C). This can be explained by the minimal uptake of PNC(−) by normal cells, as opposed to the A549 lung cancer cells that exhibited enhanced nanoparticle uptake and localization to the lysosomes (FIG. 7C). ANC (+) also exhibited various degrees of toxicity. Notably, the ANC(+) polymer-coated nanoparticles were more toxic to H9c2 (FIG. 8A), HEK 293 (FIG. 8B), and A549 (FIG. 8C) cells, since these cells exhibited increased nanoparticle internalization and lysosomal localization.

Figure 8D:
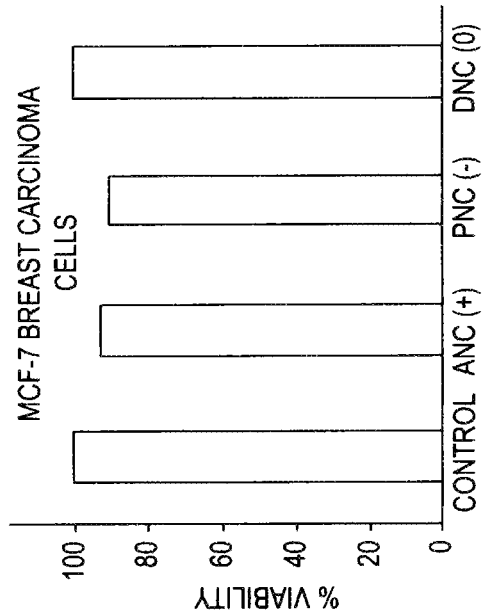
FIG. 8D is a graph showing cytotoxicity of ANC(+), PNC(−) and DNC(0) coated cerium oxide nanoparticles to MCF-7 breast carcinoma cells.
Figure 8C:
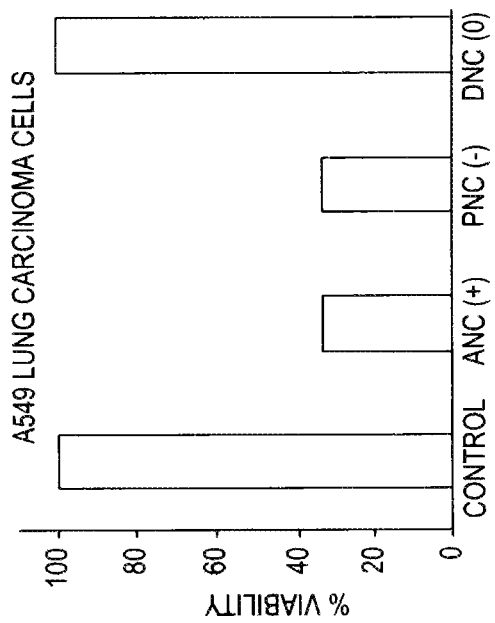
FIG. 8C is a graph showing cytotoxicity of ANC(+), PNC(−) and DNC(0) coated cerium oxide nanoparticles to A549 lung carcinoma cells.

In FIG. 8D, the breast cancer cells (MCF-7) did not show any toxicity after treatment with any of the polymer-coated nanoparticles studied, since these cells did not show any significant nanoparticle uptake.

In FIGS. 8A-8D, MTT assays show that the ANC (+) is cytotoxic to all cell lines except for the breast carcinoma cells. While PNC (−) is only cytotoxic to A549 lung cancer cells as they internalize and localized into the lysosomes these cells. DNC(0) does not show any toxicity to any of the cell lines.

Incubation of the H9c2 cardiac myocytes (FIG. 9A) and A549 lung carcinoma cells (FIG. 9B) with ANC(+) and PNC(−) in the presence of inhibitors of endocytic pathway, such as, 2-deoxyglucose and sodium azide, abrogates the cytotoxicity of the nanoparticle. FIGS. 9A and 9B confirm that an endocytic uptake of these polymer-coated nanoparticles and eventual localization to lysosomes was responsible for their cellular toxicity. Taken together, these results demonstrate that localization of nanoceria into lysosomes (an acidic cell compartment), as opposed to localization into the cytoplasm, leads to cytotoxicity by activating the oxidase activity of nanoceria within these organelles.

Example 9—Comparison of the Toxicity of Surface-Charge-Engineered Nanoceria and Iron Oxide Nanoparticles To demonstrate that the observed cytotoxicity of nanoceria is attributed to the cerium oxide core (oxidase activity) and not to the nature of the polymeric coating, we performed experiments with iron oxide particles. Specifically, DiI-labeled-aminated polyacrylic acid [IONP(+)] with a positive surface charge and DiI-labeled carboxylated polyacrylic acid [IONP(−)] with a negative surface charge were used to coat iron oxide nanoparticles.

Polymer-coated iron oxide nanoparticles have been widely used in various applications, particularly in Magnetic Resonance Imaging (MRI) with minimal toxicity. For instance, various preparations of dextran-coated iron oxide nanoparticles are used in the clinic for liver and lymph node metastasis imaging, as discussed by R. Weissleder in Liver MR Imaging with Iron Oxides: Toward Consensus and Clinical Practice. *Radiology* 1994, 193, 593-595; M. G. Harisinghani et al., in Noninvasive Detection of Clinically Occult Lymph-Node Metastases in Prostate Cancer, *N Engl J Med* 2003, 348, 2491-2499; and M. G. Harisinghani et al., in Does Contrast-enhanced Imaging Alone Suffice for Accurate Lymph Node Characterization?, *AJR Am J Roentgenol* 2006, 186, 144-148.

Figures 10A, 10B:
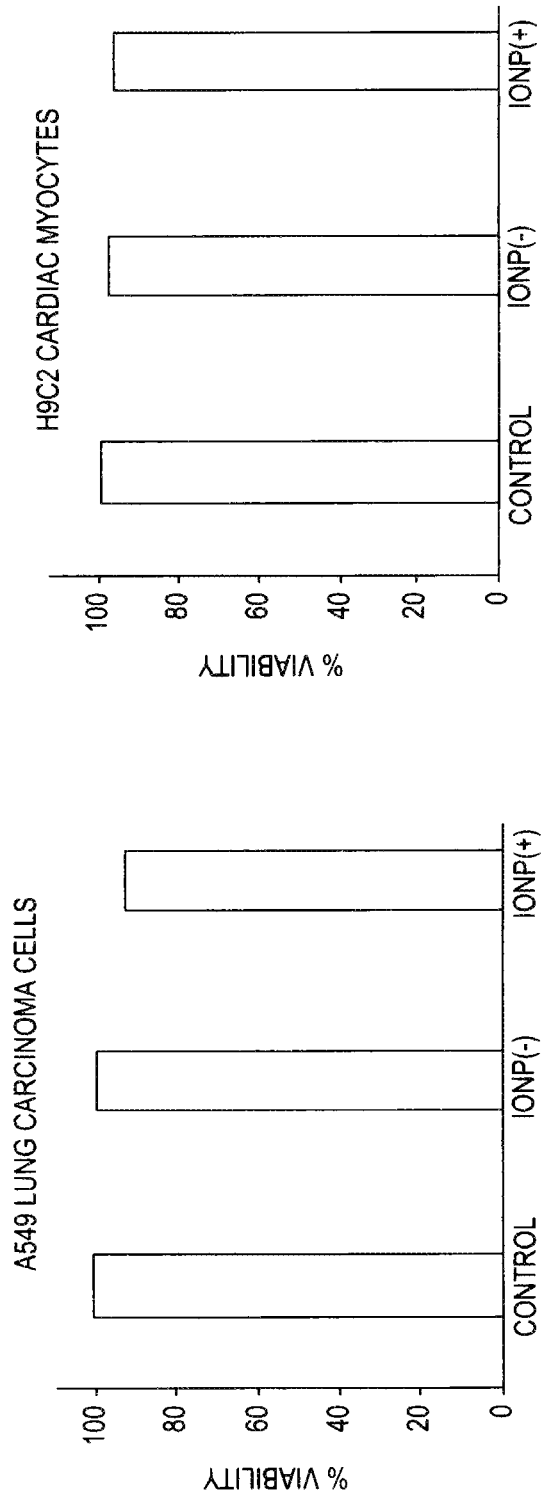
FIG. 10A is a graph showing cytotoxicity of negatively charged aminated polymer coated iron oxide nanoparticles [IONP(−)] and positively charged polymer coated iron oxide nanoparticles[IONP(+)] on A549 lung carcinoma cells.
FIG. 10B is a graph showing cytotoxicity of negatively charged aminated polymer coated iron oxide nanoparticles [IONP(−)] and positively charged aminated polymer coated iron oxide nanoparticles [IONP(+)] on H9c2 cardiac myocyte cells.

The polymeric iron oxide nanoparticles [IONP(+) and IONP(−)] were not toxic to either the transformed A549 carcinoma cell line or the non-transformed H9c2 cell line as shown in FIGS. 10A and 10B, respectively. The fact that more of the IONP(+) nanoparticles were localized into the lysosomes upon internalization in H9c2 did not seem to significantly alter the toxicity profile of the polymer coated iron oxide nanoparticles. These results are not surprising, as iron oxide nanoparticles do not possess oxidase activity, particularly at the low pH of the lysosomes. Therefore, we can conclude that the intrinsic oxidase behavior of cerium oxide nanoparticles is responsible for the nanoparticle's cytotoxicity, particularly when they localize into acidic cell compartments such as lysosomes. Cytotoxicity experiments with the neutral dextran-coated iron oxide nanoparticles were not performed since it is well established that these nanoparticles are non-toxic.

Figure 11:
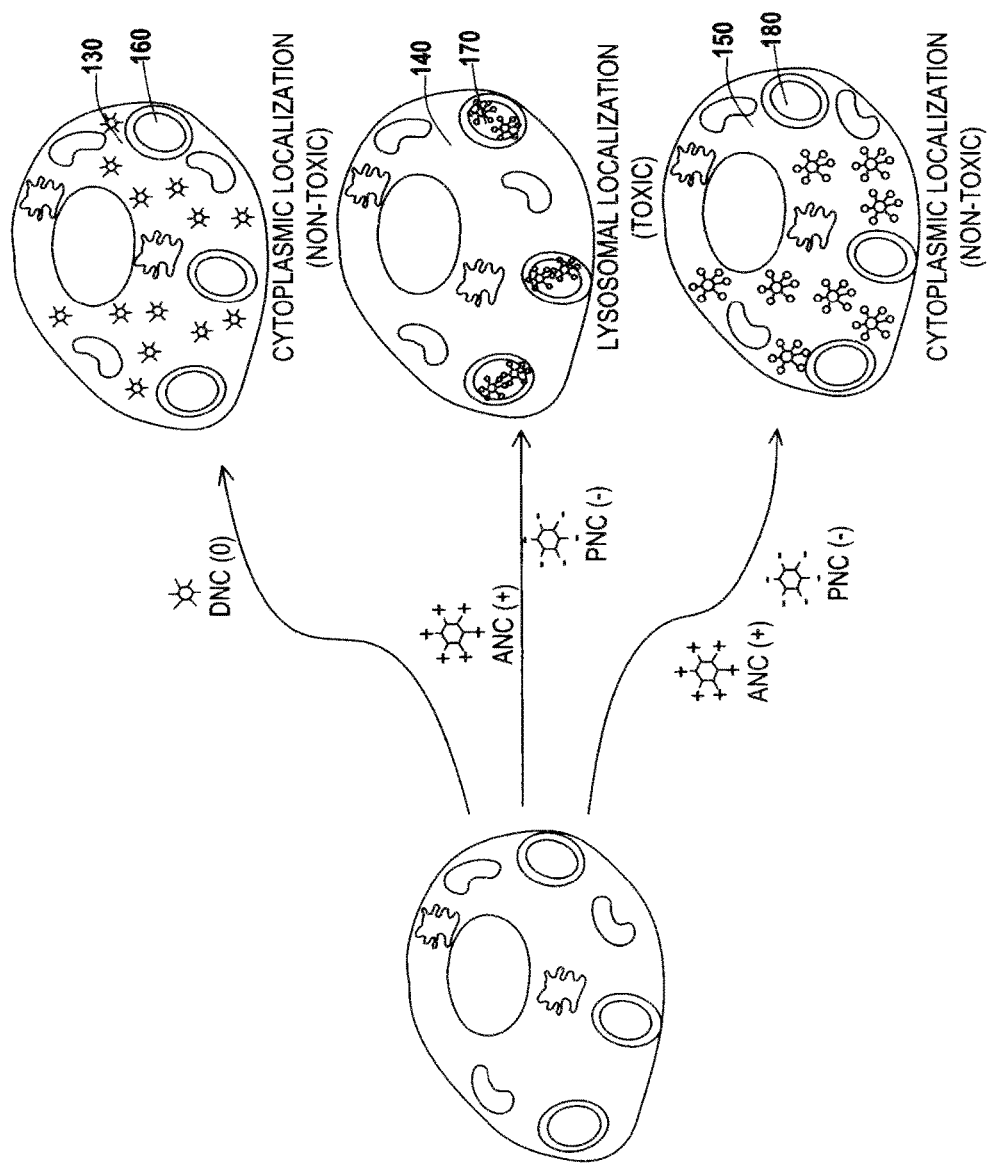
FIG. 11 is a schematic representation of polymer-coated nanoceria with different surface charges displaying cell internalization, discrete subcellular localization and toxicity profiles. Neutral DNC(0) coated nanoceria internalizes and localizes mostly into the cytoplasm 130 of cells and hence it is not cytotoxic. Whereas, ANC(+) and PNC(−) can localize either into the cytoplasm 140 or the lysosomes 170, depending on the type of cells. When the nanoceria localizes to the lysosome 160, 170, 180, the low pH of this organelle activates the nanoparticle's oxidase-like activity, exhibiting toxicity. ANC(+) or PNC(−) that localizes into the cytoplasm 150 displays no cytotoxicity.

In FIG. 11, the schematic drawing shows polymer-coated nanoceria with different surface charges displaying cell internalization, discrete subcellular localization and toxicity profiles. Neutral DNC(0) internalizes and localizes mostly into the cytoplasm 130 of cells and hence it is not cytotoxic. Whereas, ANC(+) and PNC(−) can localize either into the cytoplasm 140 or the lysosomes 170, depending on the type of cells. When ANC(+) or PNC(−) localize into the cytoplasm 150 no cytotoxicity is displayed. Thus, no toxicity was observed when polymer-coated nanoceria localized to the cytoplasm 130, 140, 150 of cells, however, upon localization to the lysosomes 160, 170, 180 the low pH of this organelle activates the oxidase-like activity of the ceria nanoparticle, exhibiting toxicity.

Materials and Methods:
Synthesis of Polymer-Coated Nanoceria Preparations [DNC (0), PNC (−) and ANC (+)].

The polymer coated nanoceria preparations, DNC(0) and PNC (−) were synthesized using the methodology described by A. Asati et al., in *Angewandte Chemie-International Edition* 2009, 48, 2308-2312 supra. Briefly, a solution of cerium (III) nitrate (2.17 g, 1.0 M, Aldrich, 99%) in water (5.0 mL) was mixed separately with an aqueous solution of either polyacrylic acid (PAA, 0.5 M, Sigma) or dextran (1.0 M, Sigma) and mixed it thoroughly using a vortex mixer. The resulting mixture was then added to an ammonium hydroxide solution (30.0 mL, 30%, Sigma Aldrich) under continuous stirring for 24-h at room temperature.

The preparation was then centrifuged at 4000 rpm for two 30-minute cycles to settle down any debris and large agglomerates. The supernatant solution was then purified from free polymers and other reagents and then concentrated using a 30K Amicon cell (Millipore Inc.). ANC (+) is synthesized directly from PNC (−). In this method, PNC (−) (5.0 mL, 1.5 mg/mL) is treated with EDC [1-Ethyl-3-(3-dimethylaminopropyl) carbodiimide] solution (28.0 mg, 30 mmol) in MES buffer (500 µL, 0.1 M, pH 6.0) followed by the drop-wise addition of N-Hydroxy succinamide (NHS) solution (22.0 mg, 30 mmol) in MES buffer (500 µL, 0.1 M, pH 6.0) and incubated for 3 minutes at room temperature. Ethylenediamine (EDA, 10 mg, 25 mmol) in DMSO (100 µL) is then added drop-wise to the final reaction mixture and stirred for an additional 3 h at room temperature.

The resulting solution was purified to remove excess EDA and other reagents usingan Amicon dialysis membrane (MWCO 30K) from Millipore. The final ANC (+) preparation (1.5 mg/mL) in DI water was stored in the refrigerator for further characterization.

DiI Encapsulation in Polymeric-Coated Nanoceria [DNC (0), PNC (−) and ANC (+)].

In order to encapsulate the DiI dye (Invitrogen) into the polymeric matrix of the various polymer-coated nanoceria, we have used a modified solvent diffusion method, as reported by S. Santra in *Small* 2009, 5, 1862-1868 supra. Briefly, to a 4.0 mL of the nanoparticle solution [1.5 mg/mL, DNC(0), PNC (−) or, ANC (+)], 200.0 µL of DiI solution [6.0 µL of DiI (10 mg/mL) in 194 µL of DMSO] was added dropwise while mixing (1000 rpm) at room temperature. Afterwards, the preparation was dialyzed (MWCO 30 K) against deionized water to remove any free DiI, and finally was dialyzed overnight in phosphate-buffered saline (1×PBS) to reconstitute the final preparation in PBS.

Characterization.

The various polymer-coated nanoceria preparations were characterized by transmission electron microscopy (TEM) to confirm the size of the nanocrystal core. TEM was performed by mounting a drop of nanoparticles on a holey carbon-coated copper 400-mesh grid (2SPI, USA) and images were taken on a FEI TECNAI F30 microscope operating at 300 kV. Surface charge on the nanoparticle was confirmed by the zeta potential measurements (Malvern Zetasizer and disposable zeta cells). FT-IR experiments were performed on vacuum dried samples to verify the surface functionalities on nanoparticles (Perkin Elmer Spectrum 100 FT-IR spectrometer). Fluorescence spectroscopy studies were done on DiI-labeled using a Nanolog HORIBA JOBIN YVON Spectrometer to confirm the DiI dye encapsulation in nanoparticles.

Cell Culture.

All cell lines in this study [lung carcinoma (A549), cardiac myocytes (H9c2), human embryonic kidney (HEK293) and breast carcinoma (MCF-7)] were obtained from American Type Culture Collection (ATCC) in Manassas, Va. The cardiomyocytes were grown in Eagle's Minimal Essential medium supplemented with fetal bovine serum (10%), sodium pyruvate, L-glutamine, penicillin, streptomycin, amphotericin B and non-essential amino acids. HEK293 cells were grown in Eagle's Minimal Essential medium supplemented with fetal bovine serum (10%) and 1% penicillin. The lung cancer cells were grown in Kaighn's modification of Ham's F12 medium (F12K) supplemented with fetal bovine serum 5%, L-glutamine, streptomycin, amphotericin B and sodium bicarbonate. All cell lines were maintained at 37° C., 5% $CO_2$ in a humidified incubator. MCF-7 cells were grown in Eagle's Minimal Essential medium supplemented with fetal bovine serum (10%) with 0.01 mg/mL bovine insulin and 1% penicillin.

Cellular Uptake of Polymer-Coated Nanoceria [DNC(0), PNC (−) and ANC (+)].

Ten thousand (10,000) cells including cardiomyocytes, human embryonic kidney cells, lung carcinoma cells and breast carcinoma cells that were seeded in petri dishes and incubated with DiI-labeled-DNC(0), DiI-labeled-PNC (−) and DiI-labeled-ANC (+) (1.0 mM), for 3 h at 37° C., 5% $CO_2$ in a humidified incubator.

Then, the cells were washed with 1×PBS and fixed with 10% formalin in 1×PBS. Afterwards, the cells were incubated with DAPI (1 mg/mL, Molecular Probes) for 10 minutes. Then the cells were washed and visualized under a confocal microscope (Zeiss LSM 510).

Inhibition of Cellular Uptake of the Polymer-Coated Nanoceria.

For these studies, 10,000 cells (H9c2 and A549) were treated with the inhibitors sodium azide (10 mM) and 2-dexoyglucose (50 mM) for 30 minutes. Then, the cells were incubated with DiI-labeled PNC (−) and DiI-labeled ANC (+) preparations (1.0 mM) for 3 h at 37° C., 5% $CO_2$ in a humidified incubator. Fixation and subsequent staining with DAPI were performed as described above. Experiments were done at 4° C. incubating the cells with the DiI-labeled PNC (−) and DiI-labeled ANC (+) preparations (1.0 mM) for 3 h.

Lysosomal Staining.

After treatment of the corresponding cell lines with DiI-labeled-DNC(0), DiI-labeled-PNC (−) and DiI-labeled-ANC (+) for 3 hours, cells were washed and incubated for 20 minutes with Lysotracker (Invitrogen) (35 nM) at 37° C., 5% $CO_2$ in a humidified incubator. Fixation procedures were performed as stated before.

Lysosomal Isolation and Oxidase-Activity Determination of Entrapped Nanoceria.

Lysosome were isolated using a previously reported procedure described by Schroter et al., in A Rapid Method to Separate Endosomes from Lysosomal Contents Using Differential Centrifugation and Hypotonic Lysis of Lysosomes. *J Immunol Methods* 1999, 227, 161-168. Ten thousand (10,000) cells (cardiomyocytes, human embryonic kidney cells, lung carcinoma cells and breast carcinoma cells) were seeded in petri dishes and incubated with ANC (+), PNC (−) and DNC(0) (1.0 mM) for 3 h at 37° C., 5% $CO_2$ in a humidified incubator.

Then, the cells were washed with 1×PBS, trypsinized and centrifuged at 1,000 rpm for 8 minutes. In order to isolate the lysosomes, cells were resuspended in an isotonic sucrose solution (1.0 mL, 0.08 M $CaCl_2$, 0.25 M sucrose, 10 mM Tris-HCl) to lyse the cells into cytosolic and organelles fractions and centrifuged at 25,000 g for 15 minutes.

Subsequently, the supernatant was carefully removed, and the pellet was resuspended in 1.0 mL 150 mM KCl (10 mM Tris-HCl, pH 7.4) followed by centrifugation at 25,000 g for 15 minutes to sediment the lysosomes. The pellet containing the lysosomes was resuspended in 200 μL of TMB (1.0 mg/mL) and incubated overnight at room temperature.

After the incubation period, the absorbance at 652 nm of the lysosome suspension was recorded.

Cell Viability Assays.

Cells (cardiomyocytes, human embryonic kidney cells, lung carcinoma cells and breast carcinoma cells) were seeded in 96-well plates at a density of 3,000 cells per well and incubated with ANC (+), PNC (−) and DNC(0) (1.0 mM) for 3 h. Then, 0.5 mM of MTT [3-(4,5-Dimethylthiazol-2-yl)-2,5-diphenyltetrazolium bromide] (Sigma) was added, followed by incubation for 24 h. After 24 h, the resulting crystals were dissolved in 40 μL of acidified isopropanol and the absorbance at 570 nm was recorded using a plate reader (Bio-TEK, Synergy HT Multidetection Microplate reader).

Discussion of Research.

The toxicity of nanomaterials depends on various factors, including the nature and chemical composition of the nanoparticle's core, mode of synthesis, size, shape and crystallinity, surface reactivity, solubility in aqueous media and degree of aggregation. Although efforts have been made to study the effect of the polymeric surface coating and surface charge on the uptake, localization and toxicity of nanomaterials, the mechanistic implications are still not completely understood. This is highly important as some nanomaterials, such as cerium oxide, may display either a beneficial (antioxidant) or toxic (oxidant) effect, depending on the pH of the compartment where they localize inside the cell. Here, we have shown that polymer-coated nanoceria displays different levels of toxicity, depending upon cellular uptake and subsequent subcellular localization. We found that when polymer-coated nanoceria internalize and localize in the lysosomes, it becomes toxic due to the acidic microenvironment of these organelles, which activates the oxidase activity of nanoceria as shown in FIG. 11.

However, lower toxicity is observed when polymer-coated nanoceria localize into the cytoplasm of cells and when is not internalized by the cells. Our results also show that the internalization, eventual localization and cytotoxicity of polymer-coated nanoceria within the cell greatly depend on the surface charge of the polymeric coating and the type of cell (cancerous versus normal). For instance, we have found that the aminated nanoceria [ANC(+)] were toxic to most of the cancer and normal cell lines studied, as these nanoparticles were uptaken and localized mostly into the lysosomes. This might indicate that nanoceria's intrinsic oxidant behaviour at acidic pH is responsible for the observed cytotoxic of the cationic polymer-coated nanoparticles [ANC(+)]. Meanwhile, PNC(−) internalized mostly into the A549 lung carcinoma cells but not significantly into any of the other cell lines studied. This observation is corroborated by the fact that no lysosomal localization and therefore no toxicity is observed in MCF-7, H9c2 or HEK293 cells treated with PNC(−).

In contrast, significant lysosomal localization and cytotoxicity is observed in the A549 cells treated with PNC(−). Surprisingly, dintinct changes in cellular uptake were observed with the dextran polymer-coated cerium oxide nanoparticles [DNC(0)]. A very disperse and diffused intracellular distribution was seen in all cell lines (cancer and normal) exposed to DNC(0), with very few of the DNC(0) localizing into the lysosomes. Therefore, the neutral DNC(0) nanoparticles were found to be non toxic to any of the cell lines studied as they localize primarily in the cytoplasm. This suggests that the observed non-toxic behavior of DNC (0) might be attributed to its significantly low entrapment into lysosomes, contrary to ANC(+). Based on these results, DNC(0) would be a great platform for further development of therapeutic antioxidant nanoagents, as they exhibit minimal toxicity. In addition, they can be effectively used in radiation therapy, since they are not toxic to normal cells. Also, as dextran-coated nanoparticles have been found to have long circulation time, similarly dextran coated cerium oxide nanoparticles can be employed as long circulating antioxidant nanoagents.

Another factor, which may contribute to the cytotoxic behavior of polymer-coated nanoceria is the type of cell line used and pH of the cell's microenvironment as reported by M. C. Brahimi-Horn et al., in Hypoxia Signalling Controls Metabolic Demand. *Curr Opin Cell Biol* 2007, 19, 223-229; J. W. Kim et al., in Cancer's Molecular Sweet Tooth and the Warburg Effect. *Cancer Res* 2006, 66, 8927-8930; P. M. Smith-Jones et al., in Early Tumor Response to Hsp90 Therapy Using HER2 PET: Comparison with 18F-FDG PET. *J Nucl Med* 2006, 47, 793-796; and M. Wu et al., in Multiparameter Metabolic Analysis Reveals a Close Link Between Attenuated Mitochondrial Bioenergetic Function and Enhanced Glycolysis Dependency in Human Tumor Cells. *Am J Physiol Cell Physiol* 2007, 292, C125-136.

The factors that contribute to the cytotoxic behavior of polymer-coated nanoceria are particularly relevant because tumor progression, increased invasion, metastasis and acidic tumor environment have been found to be interrelated, as discussed by R. J. Gillies in The Tumor Microenvironment: Causes and Consequences of Hypoxia and Acidity. Introduction. *Novartis Found Symp* 2001, 240, 1-6; R. J. Gillies et al., in Frontiers in the Measurement of Cell and Tissue pH. *Novartis Found Symp* 2001, 240, 7-19; discussion 19-22, 152-153; N. Raghunand et al., in pH and Chemotherapy. *Novartis Found Symp* 2001, 240, 199-211; discussion 265-198; N. Raghunand et al., in Acute Metabolic Alkalosis Enhances Response of C3H Mouse Mammary Tumors to the Weak Base Mitoxantrone. *Neoplasia* 2001, 3, 227-235; E. K. Rofstad et al., in Acidic Extracellular pH Promotes Experimental Metastasis of Human Melanoma Cells in Athymic Nude Mice, *Cancer Res* 2006, 66, 6699-6707; and M. Stubbs et al., in Causes and Consequences of Acidic pH in Tumors: A Magnetic Resonance Study. *Adv Enzyme Regul* 1999, 39, 13-30.

Differences between normal and tumor tissue and tumor-to-tumor variation may play a key role in dictating the antioxidant vs oxidase behavior of the polymer-coated nanoceria. Previously, we have reported that polymer-coated nanoceria displays unique oxidase-like behavior at slightly acidic pH. Therefore, in view of this oxidase-like property at acidic pH, intracellular distribution of the polymer-coated nanoceria into the lung carcinoma's lysosomes may be the reason for these nanoparticles cytotoxicity. In addition, as A549 lung carcinoma cells and most tumors have been found to have upregulated glycolysis and increased lactic acid production, this effect might further contribute towards the buildup of an acidic microenvironment, favoring nanoceria's oxidase activity and therefore sensitizing tumors towards radiation therapy.

In summary, the role of the surface-coated nanoceria and resulting surface charge influences cell internalization, subcellular distribution and differential antioxidant/oxidant activity shedding new light in delineating the mechanisms that lead to the toxicity or non-toxic properties of nanoceria.

A surface-coating that introduces a positive, negative or neutral charge to nanoceria, controls the nanoparticle toxicity.

It has been illustrated, that dextran coated nanoceria (DNC), a polysaccharide, provides a neutral surface charge to nanoceria, and it is always non-toxic. Thus, DNC creates a nontoxic nanoceria that either does not become internalized into normal cells or transformed cells, or if cellular uptake occurs, the DNC particle goes into the cytoplasm where it is not toxic.

With regard to polyacrylic acid coated nanoceria (PNC), a carboxylated polymer, provides a negative surface charge to nanoceria, and is toxic in lung carcinoma cells (A549) when subcellular localization occurs in the lysosomes, but is non-toxic in other transformed and non-transformed cells (MCF-7, H9c2 or HEK293) when cellular uptake does not occur or subcellular localization occurs in the cytoplasm.

Aminated polyacrylic acid coated nanoceria (ANC), which results from the conjugation of ethylenediamine with polyacrylic acid, is an example of a coating that provides a positive surface charge to the nanoceria, and it is toxic in normal and transformed cells (A549, H9c2 or HEK293) when subcellular localization occurs in the lysosomes, but is non-toxic in other transformed cells, such as breast carcinoma cells (MCF-7) when cellular uptake does not occur or subcellular localization occurs in the cytoplasm.

Thus, polymer-coated nanoceria with different surface charges, such as, positive, negative and neutral, display discrete subcellular localization and toxicity profiles. No toxicity was observed when nanoceria localized to the cytoplasm of cells, however, upon localization to the lysosomes, the low pH of this organelle activates the oxidase-like activity of the nanoparticle, exhibiting toxicity. The nanoceria intracellular localization is dependent on the nanoparticle surface charge and the type of cell.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of treating cancer comprising:
    contacting lung cancer cells and normal cells with cerium oxide nanoparticles comprising a polyacrylic acid coating with a negative surface charge, under conditions such that the cerium oxide nanoparticles are internalized in the lung cancer cells but not the normal cells, thereby providing a cytotoxic result for the lung cancer cells.

2. The method of claim 1, wherein the cerium oxide nanoparticles are localized in lysosomes of the lung cancer cells and exhibit oxidase-like activity in the lysosomes.

* * * * *